US006466305B1

(12) United States Patent
McBain (10) Patent No.: US 6,466,305 B1
(45) Date of Patent: Oct. 15, 2002

(54) HIGH SPEED LASER TRIANGULATION MEASUREMENTS OF SHAPE AND THICKNESS

(75) Inventor: Richard McBain, Surrey (CA)

(73) Assignee: LMI Technologies Inc., Delta (CA)

( * ) Notice: Subject to any disclaimer, the term of this patent is extended or adjusted under 35 U.S.C. 154(b) by 0 days.

(21) Appl. No.: 09/576,485

(22) Filed: May 23, 2000

Related U.S. Application Data (60) Provisional application No. 60/135,680, filed on May 24, 1999.

(51) Int. Cl.$^7$ .............................................. G01N 21/30
(52) U.S. Cl. ................... 356/3.08; 250/559.25
(58) Field of Search ............... 356/3.1, 237.2, 356/376, 511, 600, 604; 750/559.04, 559.05, 559.06, 559.23, 559.24, 559.25

(56) References Cited

U.S. PATENT DOCUMENTS

| | | | |
|---|---|---|---|
| 3,983,403 A | * | 9/1976 | Dahlstrom et al. .......... 250/560 |
| 4,803,371 A | * | 2/1989 | Durland ...................... 250/560 |
| 4,937,445 A | | 6/1990 | Leong et al. |
| 4,939,379 A | * | 7/1990 | Horn ........................... 250/560 |
| 5,734,172 A | | 3/1998 | Pryor et al. |
| 5,753,931 A | * | 5/1998 | Borchers et al. .......... 250/559.2 |
| 5,811,827 A | | 9/1998 | Pryor et al. |
| 5,949,086 A | * | 9/1999 | Reponen et al. ....... 250/559.25 |
| 5,963,328 A | * | 10/1999 | Yoshida et al. ............. 356/371 |

\* cited by examiner

*Primary Examiner*—Thomas H. Tarcza
*Assistant Examiner*—Deandra M. Hughes
(74) *Attorney, Agent, or Firm*—Paul Smith Intellectual Property Law; Paul Smith (57) ABSTRACT

This application is concerned with laser triangulation sensors for object dimension and position determination, and in particular, more effective measurement of object shapes and/or thickness using laser triangulation sensors having multiple projected laser beams and at least two linear or matrix array cameras to view the images of light reflected from the object due to the beams impinging on the object surface. Besides disclosure of the basic operation of "multipoint" sensors of this type, novel methods and apparatus are also disclosed to assure function of the device even with objects, such as lumber, having pronounced protrusions and depressions in their surface.

28 Claims, 11 Drawing Sheets

FIG. 6a
CALIBRATION FOR CAMERA 510

FIG. 6b
CALIBRATION FOR CAMERA 511

FIG. 7 AMBIGUITY RESOLVER FLOW

HIGH SPEED LASER TRIANGULATION MEASUREMENTS OF SHAPE AND THICKNESS

This application claims benefit of U.S. Provisional Application No. 60/135,680 filed May 24, 1999

CROSS REFERENCES TO RELATED CO-PENDING APPLICATIONS BY THE INVENTOR

None

FEDERALLY SPONSORED R AND D STATEMENT

Not Applicable

MICROFICHE APPENDIX

Not Applicable

FIELD OF THE INVENTION

This application is concerned with triangulation sensors for object dimension, shape, thickness and position determination, especially at multiple locations on fast moving objects such as moving boards 28 feet long at 3 boards per second. Particularly described are, multiplexed and/or "binocular multipoint" sensors having multiple projected laser beams and at least two linear or matrix array cameras to view the images of the beams on the object. The invention discloses novel methods and apparatus to assure function of the device even with objects, such as lumber, having pronounced protrusions and depressions in their surface which otherwise can produce ambiguous answers unless the individual laser beams are sequentially illuminated in a time consuming manner.

BACKGROUND OF THE INVENTION

Laser triangulation sensors are exemplified by U.S. Pat. No. 5,734,172 or 5,811,827 by Pryor et al., entitled Method and apparatus for electro optically determining the dimension, location and attitude of objects,. These patents discuss projection of zones of light from laser or other sources on to the part, the zones being spots, lines, grids or other patterns, and further disclose a "Binocular" arrangement using two detector array cameras to determine the position of images of said zones to sub pixel resolutions, each camera disposed on opposite side of the laser beam projection axis, in order to better deal with surface curvature and light reflection characteristics.

Leong et al, U.S. Pat. No. 4,937,445, entitled Apparatus for determining the distances of points on a surface from a reference axis, illustrates the use of a large number of beams, and briefly discusses problems observed in their use. Leong discloses the necessity to segment the detector array using a plurality of pre-defined zones positioned to receive respective individual returned images, which acts to allow discrimination against return images which have dropped out due to out of range conditions.

Leong et al also discloses a two camera variant in FIG. 3 of his invention, where two cameras each are set up to view a different set of projected beams on the surface. However, this is in effect a set of Siamese twinned single systems, and Leong et al do not appear to make use of this arrangement as in the binocular embodiments of the instant invention to facilitate resolution of image confusion ambiguity or other undesirable conditions caused by the surface condition of the object, which may be, for example, a moving board, or log.

It is noted that in the following discussion, the word "laser" is meant to connote not only the laser device itself of whatever kind (typically a semi-conducting diode laser), but also any associated optics and power sources needed to assure that reliable optical energy can be delivered to a zone on the surface of the object to be measured. Typically, but not necessarily, such a zone is produced by focusing the radiation emanating from the laser to a small zone at the mean point of object location in the laser projection direction.

It is also noted that the term "CCD" in this application applies to all photo-detector arrays of what ever type. While the preferred detector array to date has been a CCD, or charge coupled device, type array (for example a Reticon 1 024C linear CCD type), it is anticipated that other array types can be used, such as CMOS types and that they can be sequentially scanned or randomly scanned—even pixel by pixel.

SUMMARY OF THE INVENTION

Laser triangulation sensors projecting multiple zones on an object which can be viewed by one photo-detector array camera operating at high speed, have found favor in industry, particularly the lumber industry where, for example, requirements exist to determine shape, thickness or local contour of 28 foot long boards moving sideways on chain conveyors at 3 boards per second, in order to control the saws used to trim the boards of non conforming stock.

Multipoint sensors, such as shown in Leong et al referenced above, have however, severe disadvantages on irregular shaped wood (increasingly the norm), in that ambiguous data can be obtained due to obscuration of projected zones in the triangulation viewing direction, typically along the object longitudinal axis. Using prior art techniques, the ambiguity problem limits accurate mensuration at high speed, increasingly an issue for modern lumber processing and manufacturing applications.

In the invention herein, two methods are disclosed to obviate the problem, which may also be used in combination if desired. First, To obviate ambiguity problems, multipoint triangulation with collimated individual lasers(or other light sources) is used in various advantageous embodiments to illuminate multiple positions on an object in a manner that allows the data to be interpreted (Alternatively, but less advantageously, a single beam can be split in to multiple beams. ). The lasers in a first embodiment herein are not all energized at once, but rather only those lasers which produce unambiguous readings are energized at any one time. By repeated sequential interrogation of the detector array using the different zone sets imaged, at the end of the process after all lasers have been energized, all zones and the resulting profiled points desired can be examined- this however, at the cost of multiple camera frames and lost time.(resulting in less spatial resolution of object shape or thickness variation for example, for any objects traveling at a given rate).

In a second set of embodiments, a more sophisticated and faster approach is disclosed which utilizes a binocular pair of photodetector array based or other TV cameras (with either line or matrix arrays)to observe the projected zones on the object (typically laser spots or short lines). Unlike Leong, each camera observes all, or substantially all of the projected zones. One or more algorithms are used to determine validity of data coming from each projected zone.

GOALS OF THE INVENTION

It is a goal of the invention to provide a triangulation device, employing at least one photodetector array camera and projecting on an object multiple projected laser or other light zones, which overcomes the ambiguity caused by object surface discontinuities while operating at the highest possible operational speed, with acceptable accuracy and at reasonable cost.

It is also a goal of the invention to provide such a device having multiplexed light sources which are energized on different scans of said camera or cameras, and to provide various mechanisms for optimizing the range, speed, resolution, and other attributes of such a device.

It is a further goal of the invention to provide a binocular sensor device comprised of at least two photodetector array based cameras for viewing all (or substantially all) projected zones on the object at once, and for discerning from comparison of data obtained from the cameras the range data corresponding to each zone, even in the presence of object occlusions, obscurations, or areas of unusual reflectance.

It is a still further goal of the invention to make use of unique triangulation geometry for each camera, multiplexing arrangements, array scan directions, and other sensor configurations to aid in discerning the correctness of data in the presence of object data ambiguity It is also a goal of the invention to provide a method for measuring the location more than two projected zones on an object, using two cameras to view said zones, said cameras each viewing a field encompassing all zones projected and wherein one camera is used to confirm that the same number of zones are seen as the number seen by the other camera It is also a goal of the invention to provide a method for measuring the location of a plurality of points on an object wherein a look up table of calibration values seen by each camera for each of the points projected on the object is provided.

It is also a goal of the invention to provide a method for measuring the location of a plurality of points on an object wherein the points are not all illuminated at once.

It is another goal of the invention to allow the reconstruction of object curved edges and other regions measured at high speed by using interpolated or extrapolated data, for example to fill in readings obtained.

It is also a goal of the invention to provide a method for increasing the reliability of detection of projected zones on objects with variant reflectance characteristics at different portions of their surface.

It is also a goal of the invention to provide a method for sorting of binocular arrangements in those cases where the binocular configuration is compromised due to physical size of placement constraints.

Finally it is a goal of the invention to provide a method for spacing projection sources such as lasers with consideration of operating window regions of the segmented output of one or more detector arrays.

BRIEF DESCRIPTION OF THE DRAWINGS

FIG. 1b illustrates an array output of such as sensor, while

PREFERRED EMBODIMENTS

FIG. 1

FIG. 1 here presented is similar to that of the Leong et al reference above, though it employs discrete lasers as illumination sources. This is much more useful as it allows higher power per projected zone on the object surface, and easier modulation of the zones on and off (or to other power levels). It is of use in profiling the shape or thickness of objects in multiple sections, such as desirable for determining parameters of ostensibly flat boards in sawing operations in lumber mills.

Figure 1A:
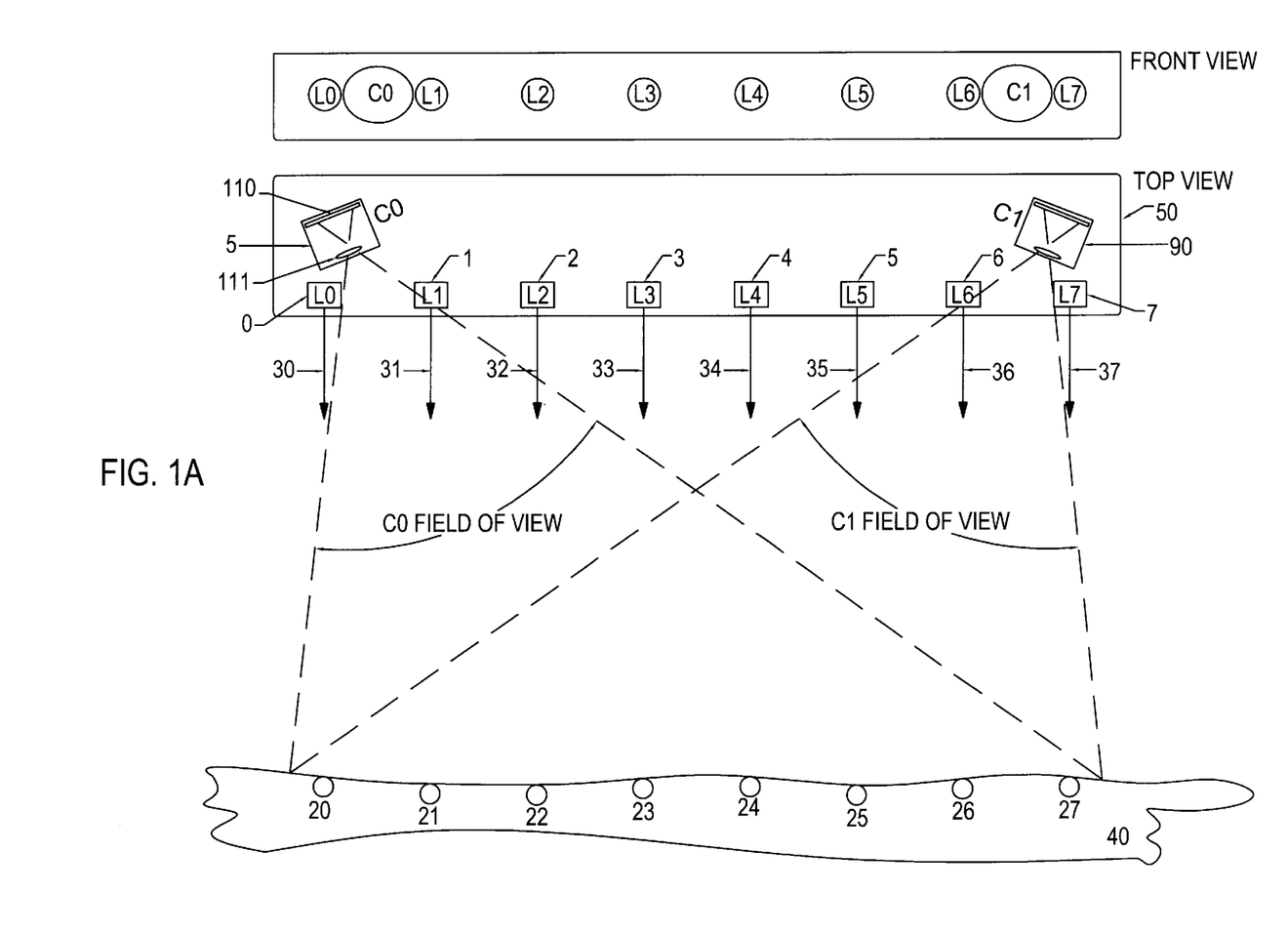
FIG. 1a is a simplified, partly diagrammatic side view of a multi-laser single camera or binocular optical apparatus comprising a preferred embodiment of the invention, in which 8 projected laser zones are directed at the object.
Figure 1B:
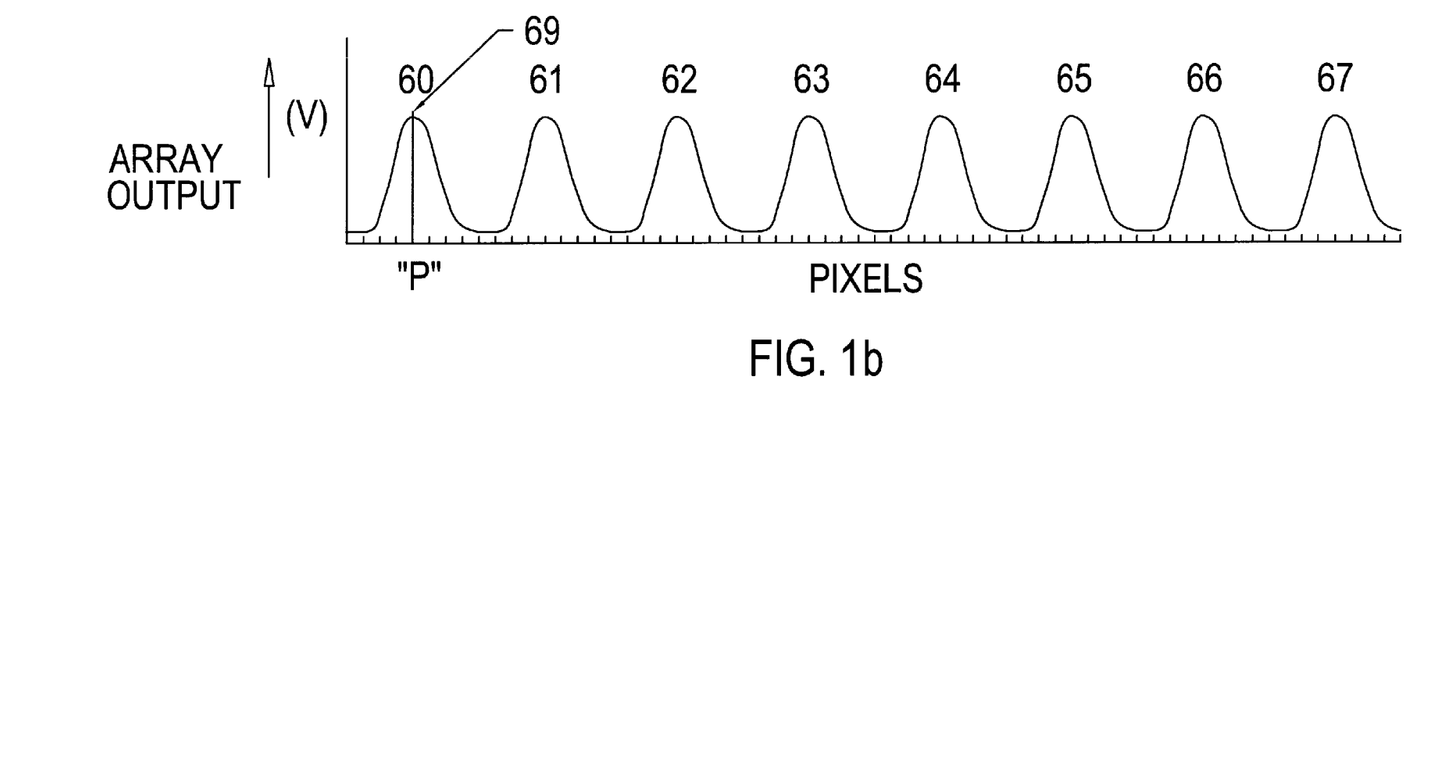

When a camera 5 (comprising a photodetector array such as 110 and lens 111) is oriented so as to be in the same plane as the projected zones 20–27 on the object 40 from laser beams 30–37 (generated by lasers 0–7), the distance of the object 40 from each discrete laser illumination point on the scan head 50 can be determined via triangulation, as discussed in the prior art references above. Measurement can be achieved for example using either in a triangulation model calculation, or via empirically determined a look-up table, based on the position on the array of zone images 60–67 received, as illustrated in FIG. 1b. For example, array pixel element value "P" corresponding to the centroid 69 of zone image 60, can be stored in a look up table to mean a sensor to object distance of 15 inches, say.

An optional second camera 90, (shown in dotted lines), typically located on the opposite side of the sensor housing from camera 5, may be provided to form a "binocular" system comprising two cameras. However, unlike the invention of Leong et al, in this case it is preferred that each camera able to see all or substantially all projected zones (in the absence of object shape problems). The function of this camera is described in FIG. 5.

Figure 1C:
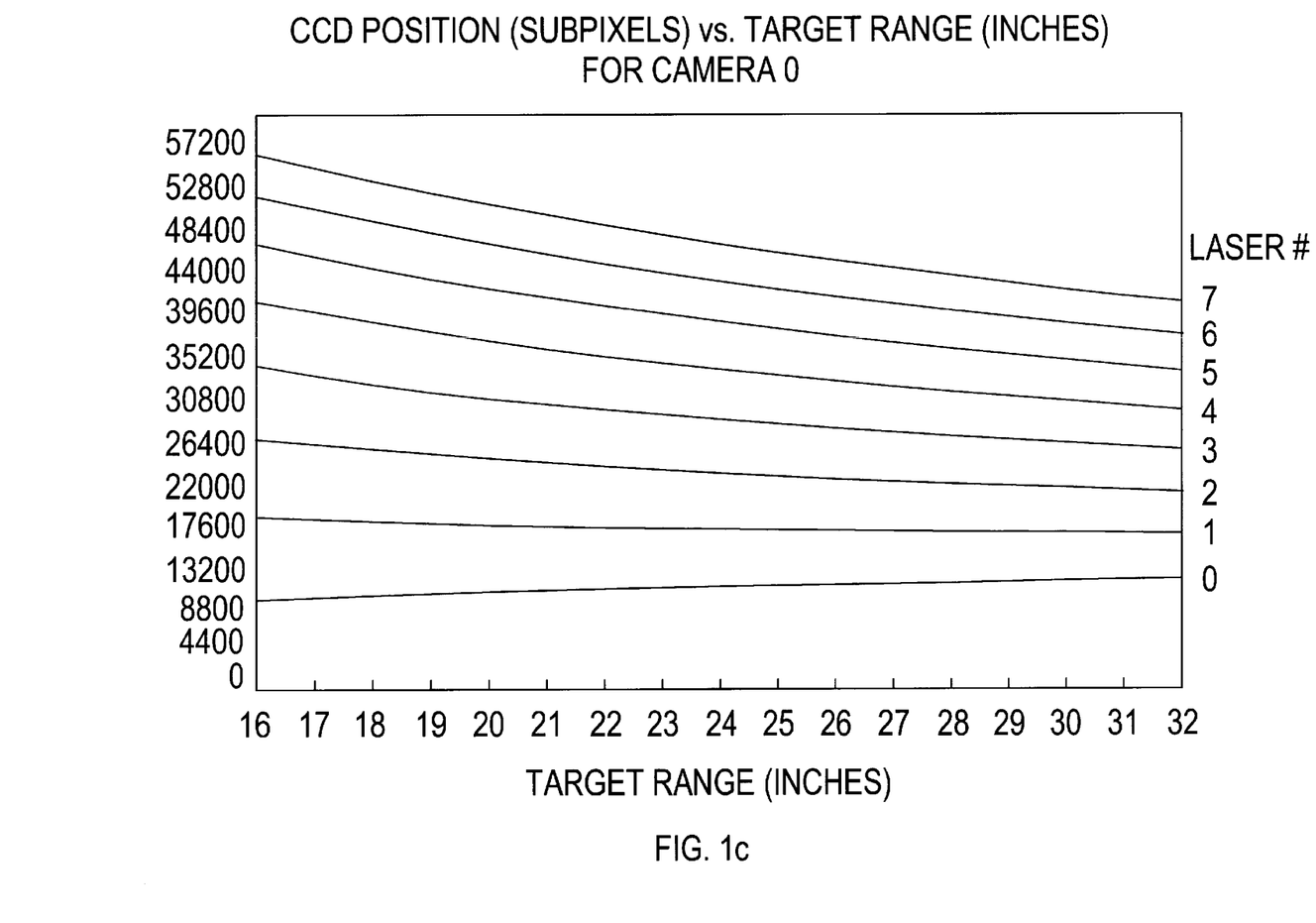
FIGS. 1c and 1d are calibration graphs of such a binocular sensor, showing the relationship between range, CCD spot position and laser number.

FIG. 1c. provides an example calibration graph for the first camera 5, provided as a result of calibrating the sensor by positioning an object at a variety of known distances and recording the resultant position of centroids on the array, for each laser, 0–7.

Figure 1D:
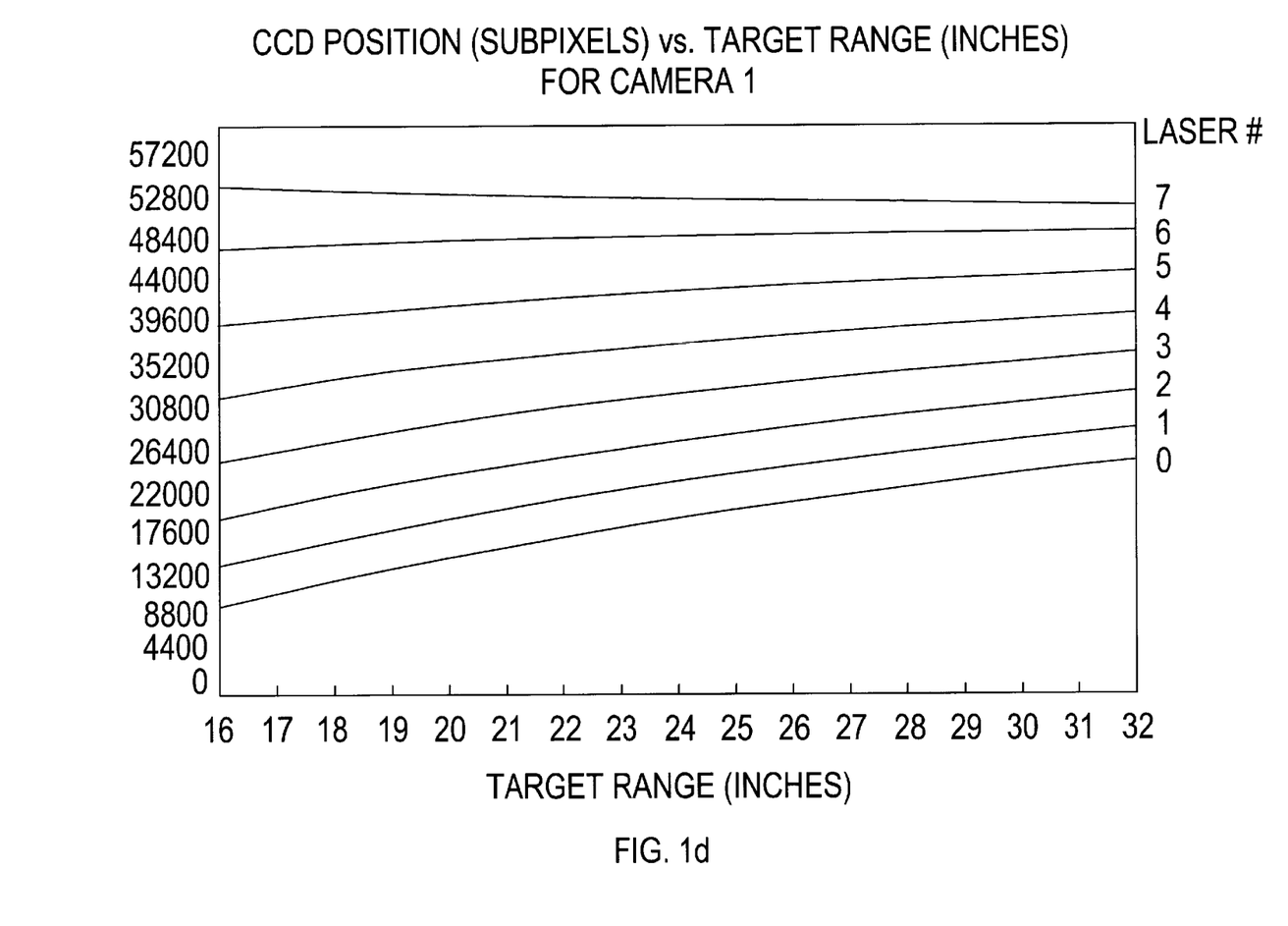

FIG. 1d. provides the calibration graph for the optional second camera 90.

Sub-pixelization and the Invention

It should also be noted that typically such measurements require sub-pixelization to achieve the accuracies needed. Mechanisms to do this are described in U.S. Pat. No. 5,734,172 referenced above as well as in U.S. Pat. No. 4,394,683

Such sub-pixelization has to run at high speeds in order to not itself cut the scan rates anymore than absolutely necessary. This criteria is met by sub-pixel triangulation techniques described in each of the referenced patents. For example, in FIG. 1 it is preferred to look at the second derivative of the calculated (either analog or digitally) of the generally Gaussian shaped spot (or other zone) image on both sides of the image of the zone and to calculate the centroid in the direction of array scan, or other scan direction desired. However any other means for determining the centroid or other effective measure of the projected zone image position can be used.

Figure 2:
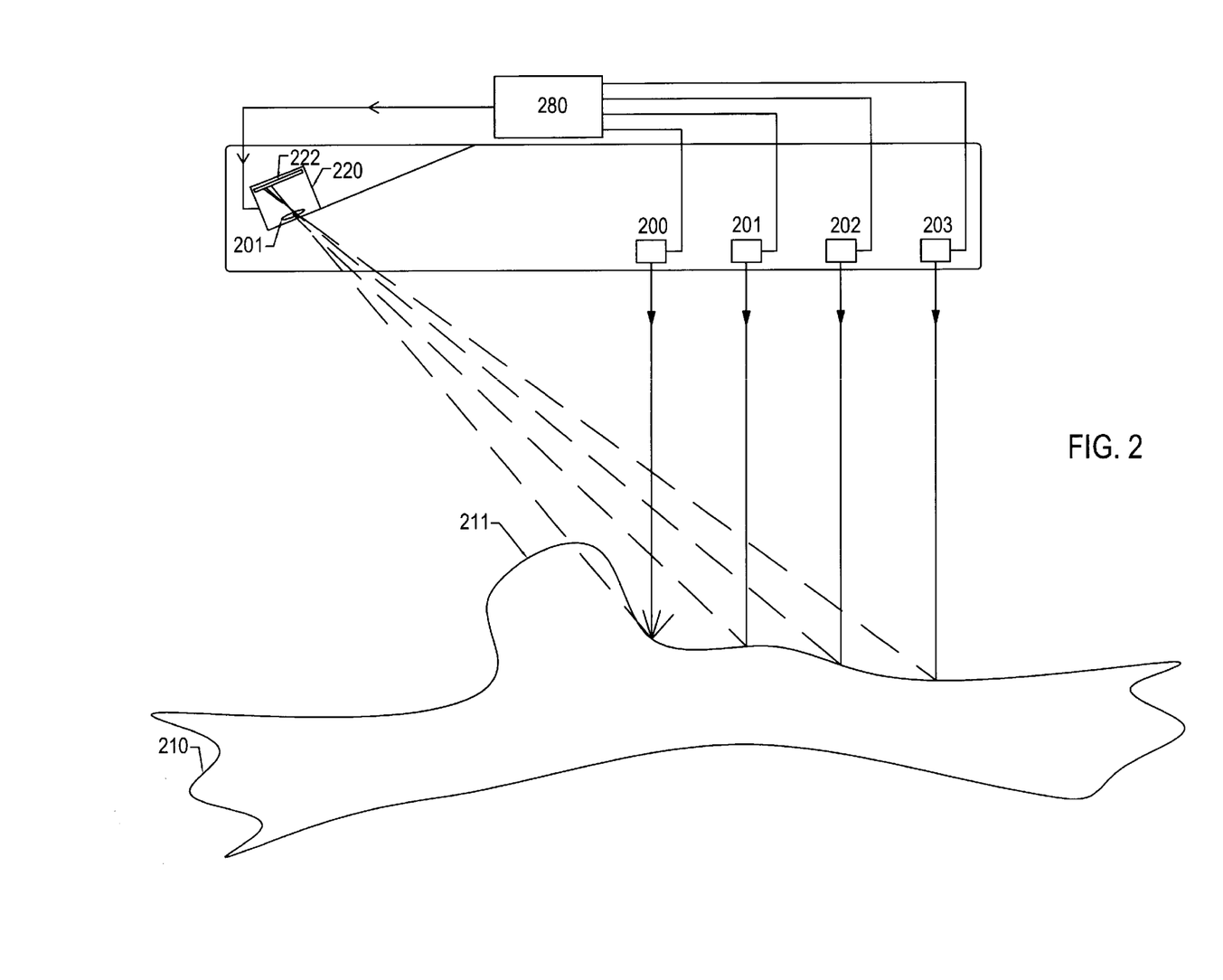
FIG. 2 is an illustration of one example of the ambiguity problem.

FIG. 2 Ambiguity illustration

The triangulated distance calculation in FIG. 1 assumes that one knows in advance which laser caused the particular illumination of the zone on the object detected in the image of same by the array and its processing electronics and software. In practice, when using only one lens and array camera per set of multiple lasers, an ambiguity in determining the lasers beam (or other projected zone) locations on the object corresponding to the particular received images is possible . For the range of positions they may be detected on the CCD overlaps with other lasers present in the same CCD measurement interval or frame and one or more received impulses is missing (due to occlusion, for example) or extra (due to spurious light, example).

Multizone sensors of the kind described above have problems involved with confusion of zone images sensed. For example, In lumber scanning, some causes of "missing spots" include:

end of board, left side (i.e., first N spots missing);
end of board, right side (i.e., last N spots missing);
outward curved edge (e.g., middle N spots missing);
inward curved edge (e.g., outer N spots missing), and
spot dropout, due to occlusion of line of sight of camera, or rapid drop in reflectance (resulting in spot missing at various laser positions).

Causes such as these of missing spot images on the array used to scan the image of the projected zones on the object, combine to make unambiguous sorting of projected zones from individual laser or other sources difficult in monocular systems, especially where segmenting the CCD into unique zones for each laser cannot be employed (due to compact laser spacing, or a wide range of sensor operating distances).

FIG. 2 illustrates, in a four laser head example, the potential for ambiguity in a system such as FIG. 1 where one camera such as 220 again comprising a lens 221 and photo-detector array 222, views a number of laser spots or other zones projected on the surface of the object—in this case those of four projections 200 to 203 projected onto the surface of object 210 and viewed by camera 220.

Clearly the reflected light in the direction of the camera from the spot 200 on the object is obscured by a portion 211 (greatly exaggerated, for clarity) of the object and cannot be seen by the camera. If one simply scans over to find the location of the spot from one point of the detector array, one immediately confuses the first spot seen. That is the point "P" on the object where the laser spot 201 has impacted it is uncertain, and appears, when the array is scanned in the direction from a to b as shown in FIG. 1, to be that of spot 200, albeit at a larger range away.

While in the simplistic example shown here, one could simply determine that all of the other beams were present and accounted for and can therefore conclude what had happened. However, in a practical case where perhaps as many as six or eight beams might be used and where the surface could have depressions and protrusions in varying places one generally does not have enough information to sort this out from just these views.

Figure 3:
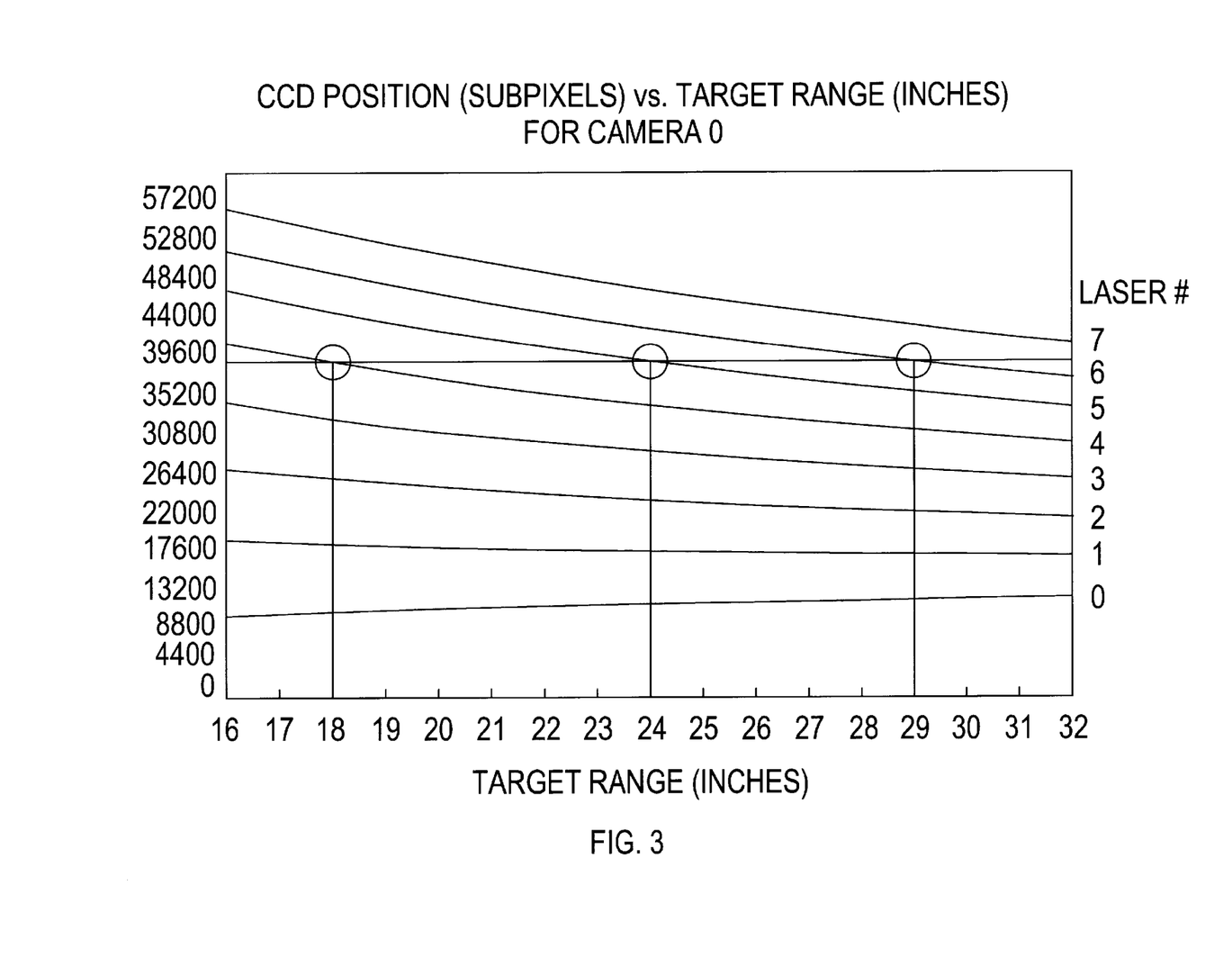
FIG. 3 is the calibration graph for one camera, illustrating the ambiguity problem.

FIG. 3

FIG. 3 shows another case of ambiguity in a graphical fashion. In the case shown, a spot at approximate (abbreviated as "~" in this disclosure) subpixel position 39600 can be caused either by an object 18 inches distance from laser 4, or 24 inches from laser 5, or 29 inches from laser 6.

It should be noted that the zones that can be projected by the beams 200 to 207 not only can be spots, such as laser spots (produced by raw, collimated, or focused laser beams) which is more simplistic, but also lines for example. These lines typically are in the direction out of the plane of the paper—which in this particular case (FIGS. 1, 2, 5 drawings), is the direction of the motion of the object.

Figure 4:
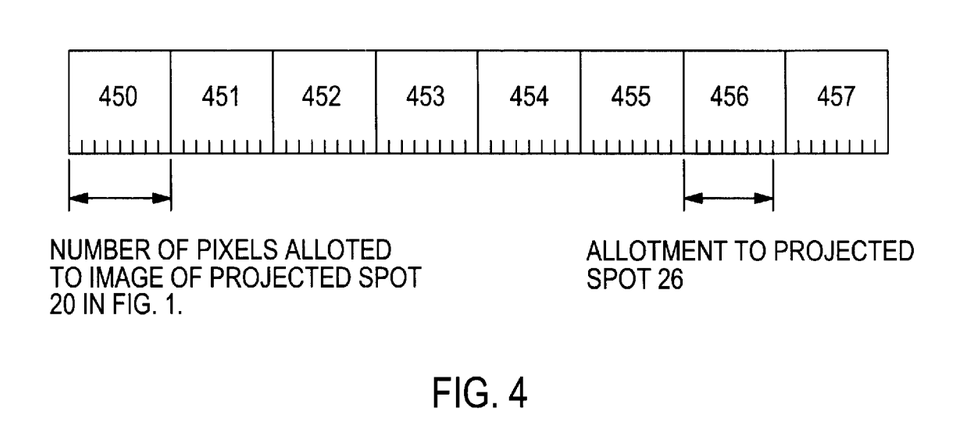
FIG. 4 is a control diagram of multiplexed sequenced laser (or other) sources and array cameras used to avoid ambiguity at a cost of increased scan time.

FIG. 4 Resolution of Ambiguity Through Multiplexing

One answer to the ambiguity problem posed in FIG. 2 is to pulse the light sources (typically laser diodes) in succession. For example the grouping, if it is considered due to the distance between the lasers let us say, four inches along the object length, for example, is not enough in one practical case (but by no means all). But in this case, eight inches in spacing between simultaneous projection points was enough for example to preclude the confusion. One could simply pulse laser 200 and 204 together, and then laser 201 and 205, etc., each set on a separate frame of data. However, in the extreme, if the surface was filled with significant undulations and perturbations, then each of the lasers would have to be pulsed independently and in this case, eight consecutive frames would be required to make the measurement.

The invention comprehends doing just this, if necessary, as a means to sort out the data, albeit at a relative loss in reading rate—problem in many cases since objects such as boards for example are moving out of the plane of the paper at significant rates and one would like to contour their surfaces. Particularly on their leading and trailing edge as they enter the zone of the sensor unit in order to see what is called "wane", which is the sloped uncut edge of the board.

It should also be noted that particularly on the sloped wane area there is a significant demand for very wide dynamic range in light gathering ability of the camera system since the reflectivity can vary both due to the form variations on the wane surface of the object and the various discoloration's that can occur. These variations are far higher than is seen on the flat uncut edge and typically they diminish rapidly. In this case it is desirable to control the laser power of the system as well as the integration time, scan rate or other variables of the detector array, such as described in U.S. Pat. No. 5,734,172. referenced above.

It should be noted that the variation of reflectance of light from the object at different parts of the object is often substantial, and the dynamic range of the photodetector array is often insufficient to account for variations in light gathered from the object unless some type of closed loop laser power control is performed. (see also FIG. 5).

Further methods for removing the ambiguity in a robust fashion are illustrated in FIG. 4 This embodiment typically requires the lasers to be multiplexed over a number of CCD (or other Photodetector array, such as CMOS for example) frames by sequencer 280, which controls both the laser pulses and the reading cycle of the detector array . However, this then decreases the effective system sampling rate to a sub-multiple of the array frame rate, and is unacceptable in applications to today's high speed processes. One way around this is to segment the array into separate reading lengths, for each laser spot (or other zone) image for example.

Segmenting of the CCD Array

Segmenting the array results in significantly limiting the minimum and maximum distance that the sensor can operate correctly (the "operating window"). This is the case where all lasers are energized simultaneously (known as non-multiplexed), and the operative output of the CCD array (such as 110 in FIG. 1a) must be segmented for example into segments such as 450 –457 shown in FIG. 4 to remove ambiguities.

For example, a typical 8 laser sensor with 6 "laser spacing has an operating window of ~7" (minimum distance =14"). Outside of this window, the laser spot imaged overlap on the CCD, resulting in ambiguities. As the spacing between lasers is decreased, the range window decreases (assuming the same minimum distance). For example array segment 450, if used in the device of FIG. 1a, to detect spot 20 projected on object 40. Similarly, each segment 451 . . . 457 would be segmented to deal with only spots 21 . . . 27 on object 40.

Minimizing Segmenting (Increasing the Operating Window of Range or Resolution) by Multiplexing Sequentially energizing lasers in separate CCD measurement intervals (frames) can increase the range, at the expense of throughput (the effective system sampling rate is now a sub-multiple of the CCD frame rate). This method is known as multiplexing. In the limit, energizing only one laser per CCD frame (fully multiplexed) provides the maximum operating range, limited only by the physical laser/CCD/lens configuration (there is no ambiguity as only one laser is on during any given measurement frame). The drawback is that full multiplexing results in the lowest throughput of all multiplexing methods.

Other patterns of multiplexing the lasers address this basic trade-off of operating window vs. throughput.

A technique I call "partial multiplexing", includes simultaneously energizing evenly spaced lasers (for example, every 3rd laser in a 24 laser sensor). By alternating the start laser in subsequent frames, all lasers can be eventually energized (within 3 frames in this example), in a period shorter than can be accomplished with full multiplexing. This method, of course, still has ambiguities outside of the operating window, however, the window size has increased due to increasing the distance between the co-energized lasers.

Figure 5:
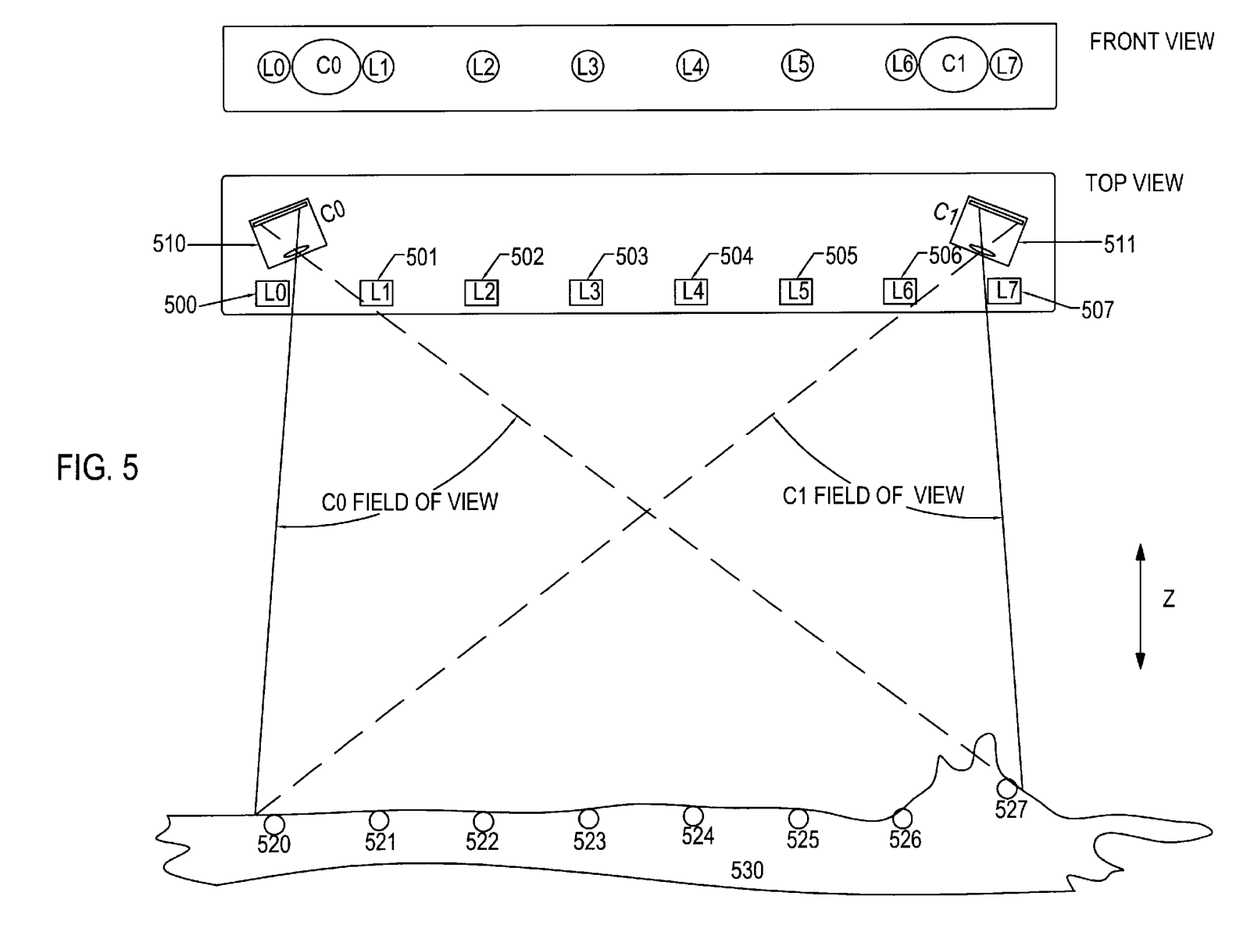
FIG. 5 is a binocular embodiment of the invention having different triangulation paths employed for analyzing data for a device having unique logic of the invention.

FIG. 5 Resolution of Ambiguity Through Binocular Image Comparison

Even with the advanced multiplexing methods disclosed above, one achieves only a fraction of the CCD frame rate, and must rely on data "reconstituted" as per the previous algorithm (thus introducing some inaccuracies). Accordingly, another method is here disclosed using a "binocular" two camera configuration (configurations with more than 2 cameras are also possible), where all lasers are energized in the same frame, thus providing maximum throughput, equal to the photodetector (CCD or other) array frame rate.

A method is now described which uses two detector arrays as a binocular vision pair in order to resolve the ambiguity present in single Photodetector array system. The major advantage is that no laser multiplexing is required, and therefore the system sampling rate is the same as the array frame rate.

This embodiment elegantly resolves the problem by using multiple cameras to simultaneously view multiple common laser illuminations via dissimilar triangulation geometry's, in order to resolve ambiguities in sorting of received laser spots.

An example configuration is shown in FIG. 5, wherein camera 510 and camera 511 both view projected spots 520 to 527 (generated by individual diode lasers 500 to 507, whose beams are not shown for clarity) on object 530.

However, as shown in FIG. 5, when object 530 has a bump or other distortion, such as 541 (here greatly exaggerated for clarity), camera 510's view of one of the laser spots, 527 is occluded. Therefore, in this 8-laser zone projection based sensor configuration, one camera, 510 in this case, sees 7 projected spots on the object, while the other camera, 511 sees 8.

Here disclosed is a system which uses one camera for triangulation, and one, for "confirmation" (the ambiguity resolver). In a preferred embodiment, they both look at all the images of the laser spot zones projected on the object The camera used for confirmation or triangulation is chosen according to the invention depending on whether it is closest to the particular laser being resolved. For example, in FIG. 5, camera 510 confirms lasers 520, 521, 522, and 523, and triangulates 524–527, while camera 511 confirms laser 524–527 and triangulates 520–523.

In calibration, a look up table (LUT) for each laser—camera combination is created. For each triangulation pixel (or sub-pixel) resolved location on the array, we store the expected confirmation pixel (or sub-pixel) position. In operation, we then search through our returned confirmation pixels or subpixels to see if we have a close match with the expected confirmation pixel or subpixel. If we find a match, then we know which laser it is and can do the triangulation based on knowing the laser projection zone assumed. If there's no match then data corresponding to the laser projection in question is classified as out of range.

In this system two cameras both have all of the zones projected on the object in both of their fields of view. The cameras are located with different triangulation geometry's. Because of the different geometry's, results for each camera will only correlate to the same distance when the pixel or interpolated sub-pixel position used in the triangulation calculation is from the same laser. This provides the fundamental "ambiguity resolver" method.

The method for correlating the results can be for example, comparing the results of calculating distances for each (sub)pixel returned for each camera (e.g., a calibrated table is stored for each camera, where each laser has distance values for all possible (sub)pixel values, or storing a table which maps, for each laser, the correspondence between one camera and another's (sub)pixels In other words, the comparison can be done in distance or in pixels. In addition, while the relation to picture elements or "pixels" is described below in relation to the zone image location, it is also envisioned to compare sub-pixel data, i.e. zone image positions on the array resolved to less than the pixel spacing.

The ambiguities are sorted by hypothesizing which laser caused the return spots as seen by each camera. For the purposes of following discussion, the calibration table uses the pixel comparison method previously described. Given a particular pixel returned from one camera, and hypothesizing a certain laser, the calibration table provides the expected pixel returned by the other camera. If such a pixel is not one of the pixels returned by the other camera, then the hypothesis is false, and other lasers may be hypothesized instead for the pixels involved.

An example is provided graphically in FIG. 6.

FIG. 6

Figure 6A:
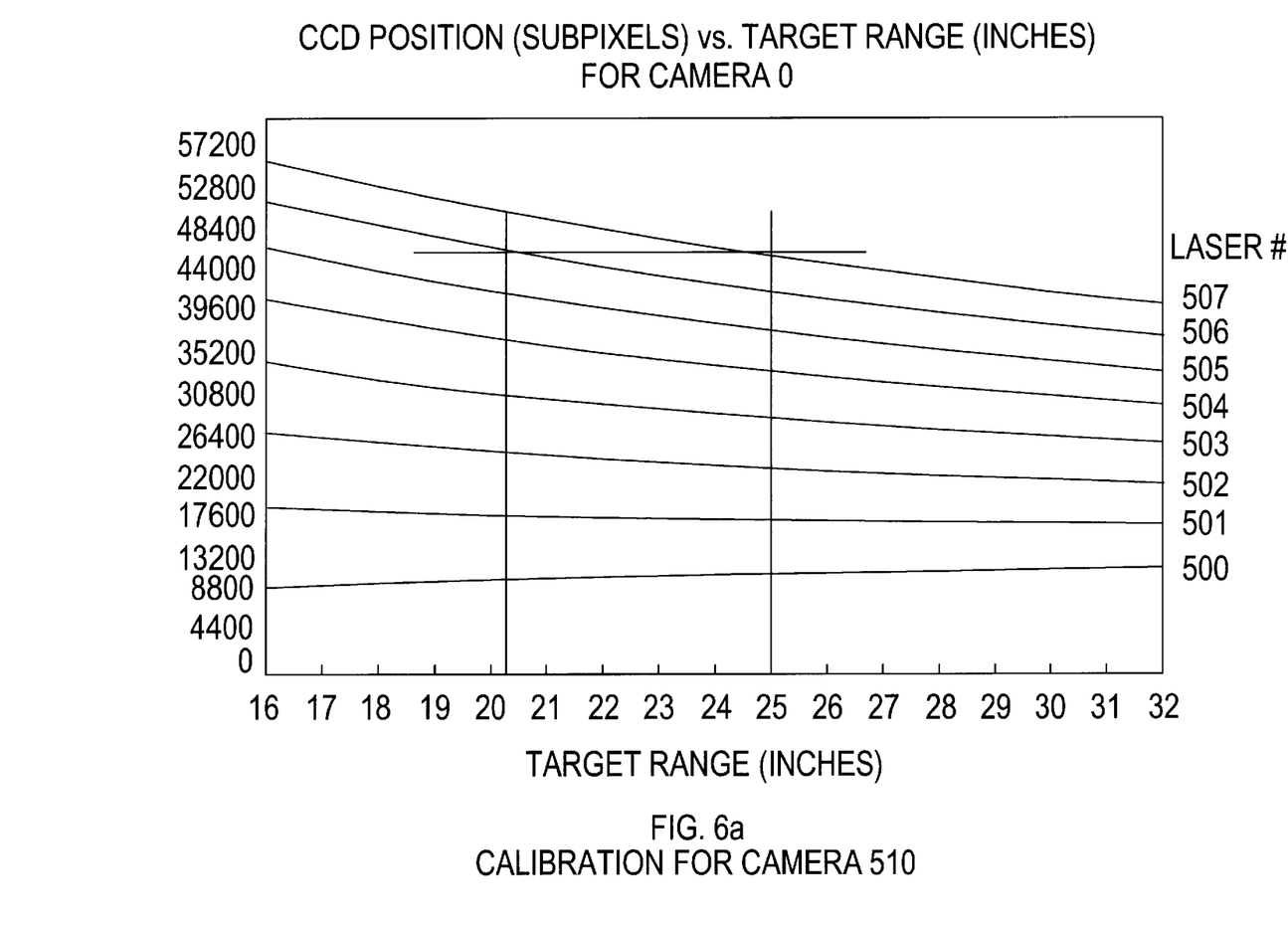
FIG. 6 illustrates calibration graphs of a binocular sensor, showing graphically the binocular ambiguity resolving method.
Figure 6B:
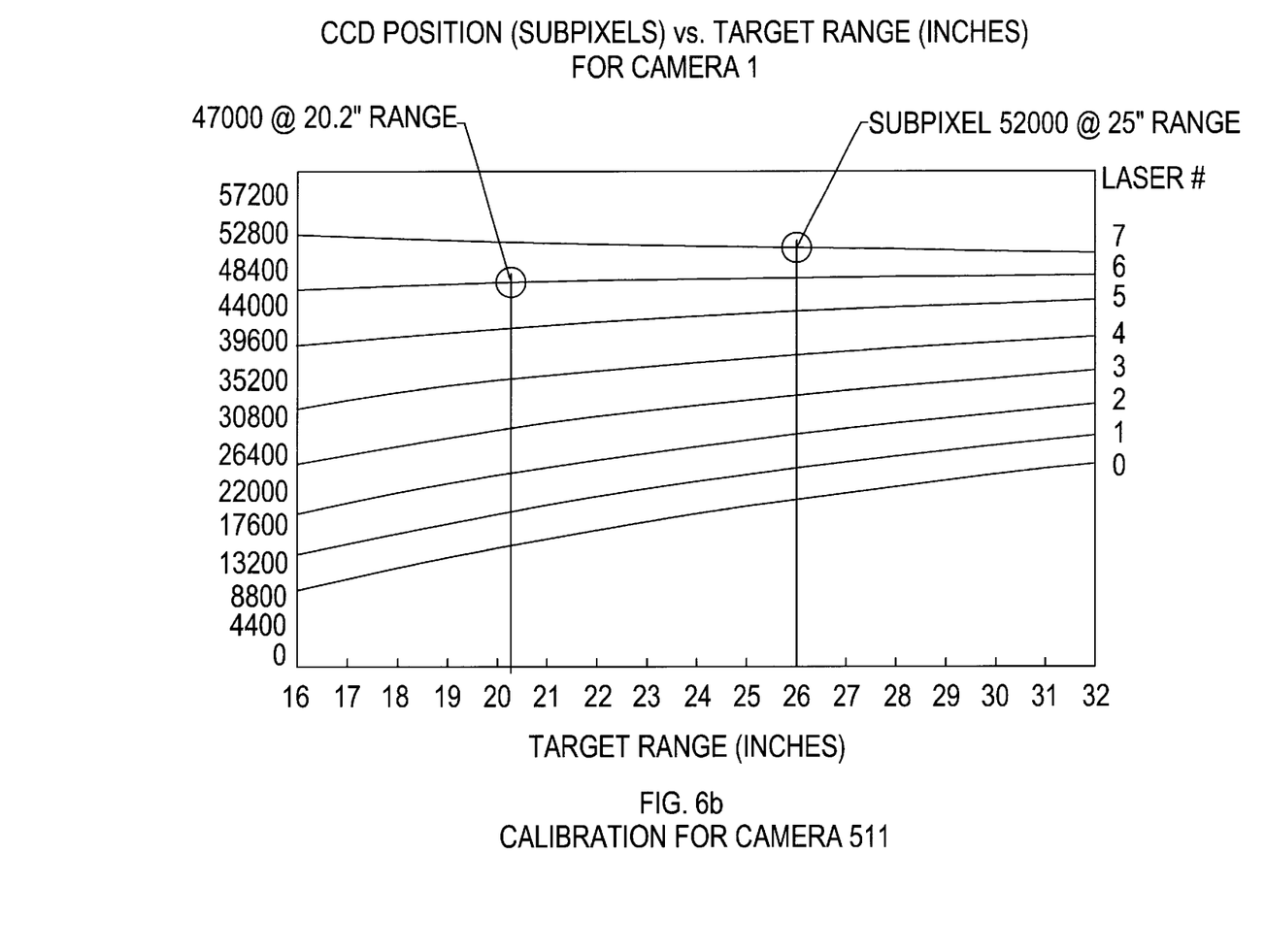

As shown in the chart of FIG. 6a, camera 510 has one centroid detected at approximately sub pixel location ~47000, resulting in an ambiguity since this reading could have been produced by either laser 506 or 507, which in this case would give two possible range readings at ~20.2 inches and ~25 inches, respectively. This ambiguity however, can be resolved, by checking the centroid returns from camera 511 (whose calibration is shown in FIG. 6b). For example, in this case the correct laser can be discerned by comparing actual returns with expected returns at the two ambiguous ranges, ~20.2 inches and ~25 inches. That is if camera 510 had two different range returns at ~47000, then from consideration of the calibration curves of camera 511, one can determine that the first (at ~20.2 inches) was produced by laser 506 (and accordingly corresponds to a given position in the x direction along object 530); a return on camera 511 indicative of a 25 inch range, would indicate that it was produced by laser 507, and accordingly corresponds to a different x location along object 530.

Put another way, where one camera's calibration curves may produce ambiguities, such ambiguities can almost always be resolved by consideration of the other camera in a binocular system where each camera views the projection of laser spots from opposite angles with respect to the spot projection direction.

In the configuration shown in the diagram, the camera with the longer triangulation baseline, such as baseline BL 521 to a particular laser spot projection direction to the camera is called the triangulation camera, (in this case camera 511) while the camera with the shorter baseline is known as the confirmation camera (in the case of spot 521, this is camera 510). The calibration table is generated which allows translation, for a given laser, from triangulation pixels to expected confirmation pixels. The expected confirmation pixel is compared with all actual pixels returned by the confirmation camera. With a close match (typically a few pixels), the hypothesized laser is correct, and the range can be calculated, based on the triangulation pixel. These two pixel locations, representative of laser spot image location on the array, one confirmation and one triangulation, are then removed from the search list, having been unambiguously resolved to the hypothesized laser. This process is repeated until all laser spot image locations on the array(s) have been resolved.

In the calibration procedure, we build a table for each laser zone projector by moving a target surface in the Z, or sensor range direction, over the full measurement range of the sensor, and recording the pixel (or subpixel) location that each laser shows up on each of the two cameras. An example table for one such laser, laser 500 in FIG. 5, is as follows:

Laser 500 table

| Range | Camera 510 pixel location | Camera 511 pixel location |
|---|---|---|
| 14" | 152 | 980 |
| 14.5" | 162 | 970 |
| 15.0" | 172 | 960 |
| 15.5" | 182 | 950 |
| . | . | . |
| . | . | . |
| . | . | . |
| 35.5" | 1045 | 302 |
| 36.0" | 1055 | 292 |

Lasers 501 through N have similar tables, but with different contents. The sensor is in this example, set up to measure object location over a range of 14 to 36 inches from the sensor.

In this table, then, is stored the relationship between the two cameras and a particular laser. Using a sensor with such a stored calibration, if one gets a return from camera 500 at pixel location 182, and a return from camera 501 at pixel 950, then it is likely that laser 500 is illuminating a surface at 15.5" from the sensor—the two camera's pixels have been confirmed by the above table to "co-relate".

Remaining Ambiguities

In practice, this technique works well, though in extreme conditions of object variation and other conditions one can experience incorrect results. For example, in FIG. 5 assume there are two lasers, 500 and 502, say, projecting zones on the object, one of which is only detectable by camera 510, and the other only detectable by camera 511 (for example, due to occlusion or inadequate reflectance, or directional reflectance of the surface). If one obtains zone images at for pixel locations 182 and 950 for the two cameras, respectively, one will incorrectly co-relate them to laser 510, when in fact they came from two separate lasers.

A trade-off also exists in the preferred embodiment, in that for packaging reasons the cameras are placed between two of the lasers at each end of the package, thus keeping the total length of the sensor as short as possible, and allowing sensor packages with 8 lasers for example, to be butted end—end with others, to create combined sensors having 16,24, 32, etc lasers so as to cover the total length of a long object, such as a 28 foot long 2×4. This arrangement results in the lasers very closely co-located with the camera which gives small triangulation angles providing very little spot image movement on the CCD over a large change in range. This can be seen from the graphs of FIG. 6a where lasers 500 and 501 constitute the "problem" lasers for camera 510. And in FIG. 6b, lasers 506 and 507 are similarly, the problem lasers for camera 511. Although these short baseline lasers are not used for measurement, but only for confirmation as pointed out above, error tolerances can result in a large range error, potentially enough to re-introduce ambiguities (due to confirmation failure).

Additionally, as a result of the trade-off, these lasers often suffer from poor detectability with their co-located camera, due to being off the center of the field of view of the camera.

Without a further processing stage, dropouts due to a lack of a detected confirmation spot (due to low detectability), or range "spikes" due to miss-sorting, occur frequently enough to cause complications in downstream data handing.

Further Processing Steps

As a further process after sorting, returns from the outer lasers are rechecked for dropouts or ranges widely outside of the current average range. If they fail the check, the return centroid positions are rechecked until a close match is found, and, if found, the range value for that laser is replaced. As the confirmation resolution to sub-pixel levels (rather than pixel levels or coarser) is not required for this method, the sometimes low detectability of projected spots from the outer lasers is counteracted.

The following defines the algorithm for post-sorting of data taken using the embodiment of FIG. 5.

```
FOR each outer laser (i=0,1,6,7)
(8 lasers total, all lasers co-located with a camera)
IF laser[i] is more than a specified amount from the average THEN
   set laser[i] = out of range
ENDIF
IF laser[i] is out of range THEN
FOR each spot centroid returned from the triangulation camera
   calculate range for this spot centroid
   IF the resulting range is within a specified amount of the average THEN
      BREAK out of inner FOR loop (keep the new range value)
   ENDIF
ENDFOR (each centroid)
ENDIF
ENDFOR (each outer laser)
```

This procedure has some potential to re-introduce ambiguities, however, this is only performed after the first ambiguity resolver method described above is performed; additionally this is only ambiguous between the lasers surrounding the camera, so the probability for incorrect solutions is minimized (that is, the total number of incorrect choices is much smaller, as all "inner lasers" have been previously correctly sorted because they don't exhibit the same level of ambiguity).

Although many types of average may be possible, the preferred embodiment is an average of all lasers, over the last 128 acceptable (that is not out-of-range) readings for each laser.

When this further process is combined with binocular sorting as disclosed previously, the resultant sensor exhibits very low rates of both dropouts and ambiguities (or "spikes"), while operating without multiplexing or windowing. Thus both system sample rate and operating window are maximized.

Figure 7:
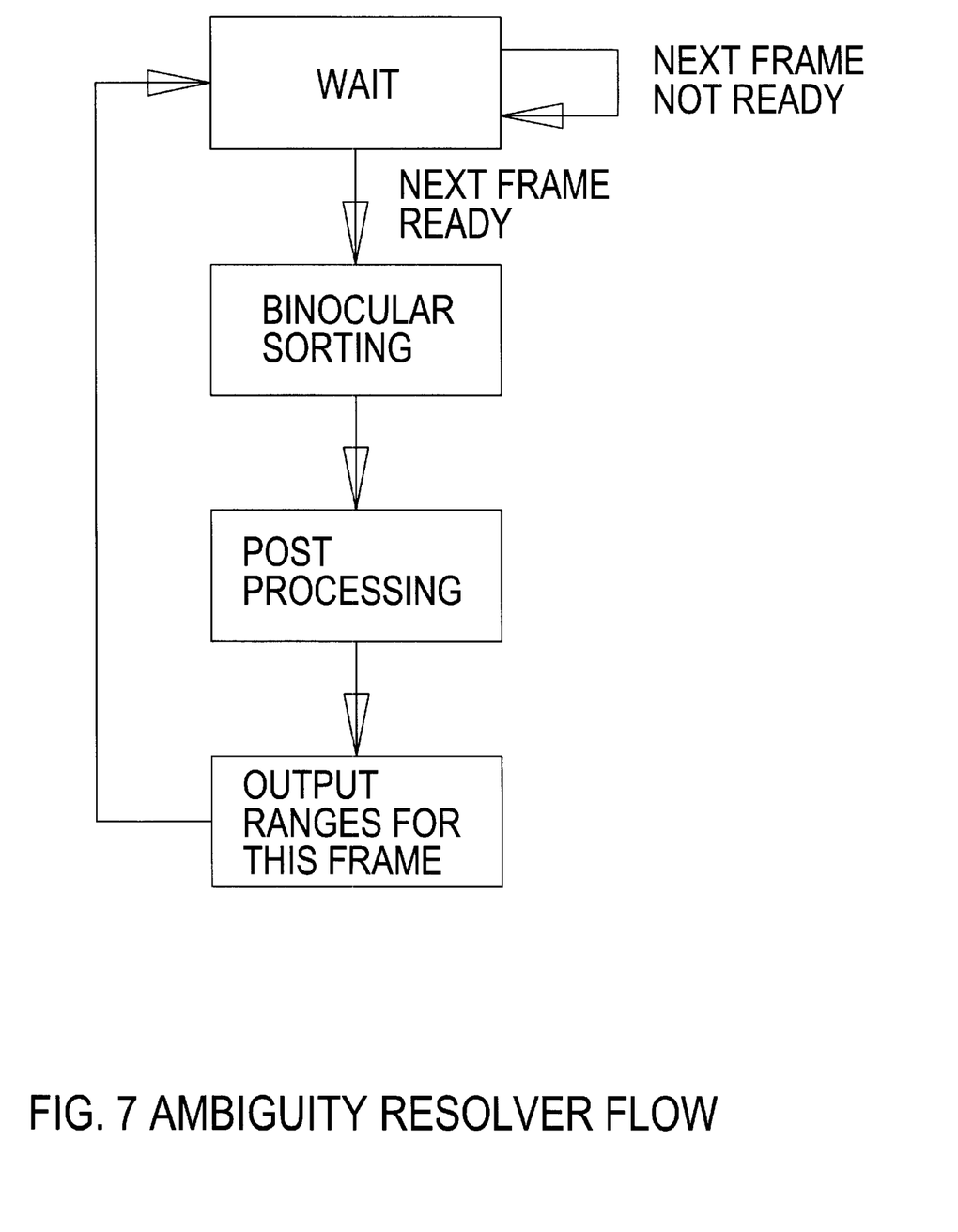
FIG. 7 is a high level flow diagram of the ambiguity resolving features of the embodiment of FIG. 5.

FIG. 7

FIG. 7 is a high level flow diagram of the ambiguity resolving features

Power Control

It should be noted that the variation of reflectance of light from the object at different parts of the object is often substantial, and in this case the dynamic range of the photodetector array is often insufficient to account for variations in light gathered from the object unless some type of closed loop laser control is performed so as to keep the light gathered by the sensor with in the dynamic range of the array.

For example, in a preferred embodiment, laser power or on-time duration is adjusted, for example with power adjusting modules for each of multiple laser projectors such as projecting zones 520 to 522 based on the light detected from the object at each zone by the photodetector array of the camera. In this case, proper resolution of the laser ambiguity problem is critical, in order to discern the correct light gathering condition for each zone and adjust it accordingly. Additionally, a faster system sampling rate allows the sensor to track changes in reflectance more closely.

The light power or other light gathering related variable of the system for each of lasers 500 to 502 above can be controlled by either of the two cameras used (in a binocular system). Typically it is controlled by the camera used to triangulate, but it also possible to average or otherwise utilize the signals from both cameras and use that data for light gathering control.

There are several other ways to use the data from each camera. For example one can average the two camera readings for a given laser spot image position, if both of these views are present. If only one of these views has all zones present, (4 in the above case) then one can just use it, and ignore the data from the other camera if desired.

Typical lasers used with the above invention are semi conducting diode lasers of visible (e.g. Red) or near IR wavelengths having output powers on the order of 10–30 mw if used on high speed board measurement.

While described mainly for use on boards and logs moving high speed, the invention herein may be used on any object for which multiple object point locations, thickness', or other dimensions are desired.

As an alternative to a two camera "binocular" arrangement, more than two cameras at different angles with respect to the laser projection axes can be used, which could be desirable in resolving extreme ambiguity in some cases.

What is claimed is:

1. A method for determining the location of a plurality of points on an object, comprising the steps of:

providing a plurality of zone projection sources;

providing at least two spaced photodetector array based cameras;

with said zone projection sources, projecting a plurality of zones on said object at a plurality of spaced positions on said object;

imaging said zones on said object with each of said cameras to provide zone image data, each of said cameras viewing a field encompassing all zones projected; and, determining from said zone image data, the location of said points on said object.

2. The method of claim 1 wherein a first one of said cameras is used to confirm that the same number of zones are seen on the object as the number seen by a second one of said cameras.

3. The method of claim 1 wherein the optical axes of said cameras are separated by an acute angle.

4. The method of claim 1 wherein said zone projection sources are lasers.

5. The method of claim 1 wherein said zones are spots.

6. The method of claim 1 wherein said zones are lines.

7. The method of claim 2 wherein the closest zones to said second camera are confirmed by said first camera.

8. The method of claim 2 wherein said first and second camera roles can be interchanged.

9. The method of claim 1 wherein said laser power is controlled to allow operation over a wide range of object reflectivity conditions.

10. The method of claim 1 wherein said camera is controlled to allow operation over a wide range of object reflectivity conditions.

11. A method for measuring the location of a plurality of points on an object, comprising the steps of:

i. providing a plurality of zone projection sources;

ii. providing at least two spaced photodetector array cameras to determine the position of images of said zones;

iii. with said zone projection sources, projecting less than the totality of said plurality of zones on an object, said zones being spaced on said object;

iv. imaging the zones on said object with said cameras, each of said cameras viewing a field encompassing the totality of all zones projected;

v. determining, from the image of said zones on said arrays of said cameras, the location of said object points corresponding to said zones; and, vi. repeating steps iii-iv until all zones have been illuminated.

12. The method of claim 11 wherein a group of said points are illuminated simultaneously, said points being spaced such that other points to be illuminated at a later time are spaced in- between.

13. The method of claim 11 wherein said zone projection sources are lasers.

14. The method of claim 11 wherein the closest zones to a first one of said cameras are confirmed by a second one of said cameras.

15. The method according to claim 11 wherein said first and second camera roles can be interchanged.

16. The method of claim 11 wherein said projection source or camera variables are controlled to allow operation over a wide range of object reflectivity conditions.

17. The method of claim 11 wherein the data from at least one of said cameras is compared with respect to previous calibration data for said camera with respect to said plurality of zone projections.

18. A method for measuring the location of a plurality of points on an object, comprising the steps of:
- providing at least two spaced photodetector array cameras;
- projecting a plurality of zones of light on an object at said points;
- imaging said zones on said object with said array cameras, each of said cameras viewing a field encompassing the totality of all zones projected;
- determining the position of said zone images on said array;
- from said determined zone image positions, determining the location of a said points on said object; and,
- confirming, by comparison of the output of said cameras, the location of one or more points determined on said object.

19. The method of claim 18 wherein said zone projection sources are lasers.

20. The method of claim 18 wherein the closest zones to a first one of said cameras are confirmed by a second one of said cameras.

21. The method of claim 18 wherein said first and second camera roles can be interchanged.

22. The method of claim 18 wherein said projection source or camera variables are controlled to allow operation over a wide range of object reflectivity conditions.

23. The method of claim 18 wherein the camera measuring said object has the largest angle or baseline with respect to any projected zone on said object.

24. The method of claim 18 wherein the camera confirming the position of a point on said object has the smallest angle or baseline with respect to any projected zone.

25. The method of claim 18 wherein the data from at least one of said cameras is compared with respect to previous calibration data for said camera with respect to said plurality of zone projections.

26. The method of claim 18 wherein the data from at least one of said cameras is accepted if within expected range values.

27. The method of claim 18 wherein the data from at least one of said cameras is accepted if within an average range of values seen on previous readings.

28. The method of claim 18 wherein the data from at least one of said cameras is replaced with previously determined data.

* * * * *